United States Patent [19]

Yorozu

[11] Patent Number: 4,879,105
[45] Date of Patent: Nov. 7, 1989

[54] WEAKLY ACIDIC BATH AGENTS

[75] Inventor: Hidenori Yorozu, Utsunomiya, Japan

[73] Assignee: Kao Corporation, Tokyo, Japan

[21] Appl. No.: 169,879

[22] Filed: Mar. 18, 1988

[30] Foreign Application Priority Data

Apr. 1, 1987 [JP] Japan .................................. 62-80481

[51] Int. Cl.⁴ ........................... A61L 9/04; C11D 7/00
[52] U.S. Cl. ...................................... 424/44; 424/466;
252/142; 252/148
[58] Field of Search .................. 252/142, 541, DIG. 5;
424/44

[56] References Cited

U.S. PATENT DOCUMENTS 2,739,130  3/1956  Combs ................................. 252/542
4,666,707  5/1987  Euguchi et al. ...................... 424/44

Primary Examiner—Paul Lieberman
Assistant Examiner—John F. McNally
Attorney, Agent, or Firm—Oblon, Spivak, McClelland, Maier & Neustadt

[57] ABSTRACT

A weakly acidic bath agent comprising carbon dioxide or a carbon dioxide-generating substance and nicotinic acid or a derivative of nicotinic acid represented by the general formula

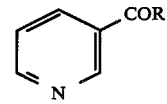

wherein R represents a group - $OR_1$, in which $R_1$ is a hydrogen atom, a saturated or an unsaturated hydrocarbon group having 1 to 10 of carbon atoms, or benzyl group.

The bath agent of the invention exhibits a favorable effects such as prevention of roughening of human skins, promotion of blood circulation, sensation of body warmth and dampishness of the skins, absence of chill after bathing and the like.

9 Claims, No Drawings

WEAKLY ACIDIC BATH AGENTS

BACKGROUND OF THE INVENTION

(1) Field of the Invention

The invention described herein relates to a weakly acidic bath agent or bath-additive preparation with a novelty. Particularly the invention relates to a weakly acidic bath agent having an excellent effect of preventing roughening of human skins and an effect of excellent feeling in bathing.

(2) Description of the Prior Art

Traditionally, bath agents are prepared by incorporating a fragrance, a colorant, a plant essence, an organic acid and the like into a mixture consisting of inorganic salts such as salt cake (crystalline sodium sulfate), borax (sodium borate), carbonates and the like and sulfur. Such bath agents are used with objects of giving a scent and/or color tone to the bath water and—causing lively circulation of blood by an adequate stimulus given to the skin thus to promote restoration from fatigue and metabolism. Among such bath agents, a group of effervescent bath agents comprising a carbonate and an acidic substance is known. They have an object of uplifting the feeling of relaxation and refreshment by bubbles of carbon dioxide gas in the bath thus to increase pleasantness of bathing.

However, the prior art effervescent type bath agents are neutral or weakly alkaline in nature so that the carbon dioxide bubbles function only mechanically for sensation due to the almost complete undissolubility of the generated carbon dioxide gas in water and - fugaceousness of it in the air.

The inventors have formerly provided bath agents of weakly acidic type comprising a carbonate and an acid which induce lowering of the pH of the bath to the weakly acidic level. These bath agents are capable of promoting circulation of blood and preventing chill after bathing owing to carbon dioxide retained in the bath water.

Notwithstanding the above, roughening of human skins accompanied with bathing has become a problem in recent years standing on the background of swelling of the higher aged population and the tendency to dehumidification of indoor air which cause increase of so-called dry-skinned persons.

On account of such a circumstance, an interest is directed to obtaining bath agents with an excellent effect of preventing skin roughening and an effect of excellent feeling in bathing.

SUMMARY OF THE INVENTION

The inventors have completed the present invention as the consequence of extensive studies with the object of solving the above-described problems standing on the finding that an excellent bath agent can be obtained by the addition of nicotinic acid or a derivative thereof to the conventional bath agent composition containing carbon dioxide or a carbon dioxide-generating substance.

That is, the present invention provides a weakly acidic bath agent comprising carbon dioxide or a carbon dioxide-generating substance and nicotinic acid or a derivative of nicotinic acid represented by the general formula

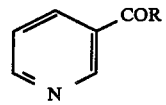
(I)

wherein said R represents a group having a formula -$OR_1$ in which $R_1$ is a hydrogen atom, a saturated or an unsaturated hydrocarbon group having 1 to 10 of carbon atoms, or benzyl group.

DETAILED DESCRIPTION OF THE PREFERRED EMBODIMENTS

In the invention carbon dioxide is incorporated in the weakly acidic bath agent in a condition of being retained by a carbon dioxide-retainable substance such as aluminosilicate and the like or in a condition of being enclosed in a container or a capsule under a high-pressure.

Aluminosilicate as used as the carbon dioxide-retainable substance should preferably be of the crystalline type but those of either the amorphous type or the semi-crystalline type may also be used. Typical examples of the crystalline aluminosilicates include naturally occuring aluminosilicates such as analcite, rhombic analcite and the like, synthetic zeolites called by the names Zeolite A, X, Y and the like and others. In particular, synthetic zeolites represented by the general formula $$(M_{2/m}O)_x \cdot Al_2O_3 \cdot (SiO_2)_y \cdot (H_2O)_z$$

in which M is an atom of metallic element with an atomic valency m, x is a positive number in the range of 0.7 to 1.5, y is a positive number in the range of 0.8 to 10 and z is 0 or a positive number, are preferred because of their low content of foreign substances such as the impurities and the like.

In the above general formula for the synthetic zeolites, the atoms of the metallic element represented by M are, for example, sodium, potassium, calcium, magnesium and the like, and those not containing water as indicated by the value 0 of the symbol z are preferred. The grain size of the carbon dioxide-retainable substances should be in the range of preferably from 0.5 to 100 $\mu$m or, more preferably, from 1 to 40 $\mu$m. The form of the carbon dioxide-retainable substances as used should preferably be, for example, fine powder as of the origin, granules, pellets and the like - with the more preference to the fine powdery form in view of the carbon dioxide-retaining effect.

Adsorption of carbon dioxide by the retaining substance is carried out for example by contact of carbon dioxide to a carbon dioxide-retainable substance. The carbon dioxide-retainable substance such as aluminosilicate used in this procedure should preferably be dehydrated in advance by heat-processing and those containing substantially no moisture are the optimum. The procedure of adsorption should be carried out in an atmosphere containing carbon dioxide with a apartial pressure of preferably not lower than 0.1 kg/cm$^2$ or, more preferably, in the range of from 1 to 10 kg/cm$^2$ with another preferred condition of desiccation. The temperature of the ambience should be kept at preferably 30° C. or lower or, more preferably, 20° C or lower during the procedure which should be continued unlimitatively with the preference to the time sufficient to attaining equilibrium.

The amount of carbon dioxide adsorbed by the CO₂-retainable substance should be preferably not less than 2 g CO₂/100 g CO₂-retainable substance or, more preferably, not less than 5 g CO₂/100 g CO₂-retainable substance.

The carbon dioxide-generating substance compounded in the weakly acidic bath agent of the invention is not restrictive on condition of generating carbon dioxide by any of reactions with particular preferences to combinations of a carbonate and an acidic substance.

The carbonate should preferably be selected from sodium hydrogen carbonate, sodium sesquicarbonate, sodium carbonate, potassium hydrogen carbonate, ammonium hydrogen carbonate, magnesium carbonate, calcium carbonate and the like which may be used alone or in combination of two or more species.

The useful acidic substance should be either an organic acid or an inorganic acid with a particular preference to water-soluble solid acids. The typical examples of the organic acids include, for example, dicarboxylic acids such as succinic acid, glutaric acid, adipic acid, pimelic acid, fumaric acid and the like; acidic amino acids such as glutamic acid, asparaginic acid and the like; hydroxy acids such as malic acid, citric acid, ascorbic acid and the like; aromatic carboxylic acids such as benzoic acid and the like and heteronucleus carboxylic acids such as pyrrolidone carboxylic acid and the like. The acidic salts of the above-listed organic acids, in particular of the dicarboxylic acids, may also be used suitably. Among the above, dicarboxylic acids selected from the group consisting of those represented by the general formula

HOOC—(CH₂)ₙ—COOH in which n is a positive integer from 2 to 4 and fumaric acid are the most preferable. Typical examples of the inorganic acids include potassium dihydrogen phosphate, sodium sulfite, and the like.

The carbonate and the acidic substance compounded in the weakly acidic bath agent of the invention should have a compounding ratio such that bath water exhibits weak acidity when the bath agent is added to the water, or that the 0.01 weight % aqueous solution of the bath agent can exhibit a pH in the range of, preferably, from 4 to 7 or, more preferably, from 6.0 to 6.7. The bath water with a pH value lower than 4 would be sometimes irritant to human skins and corrosive to the bath boiler and the like, and on the other hand the bath water with a pH value exceeding 7 would not be sufficient to exhibit the expected effects of the invention. That is because the effects of carbon dioxide in the invention is based on the principle that, in the events of the pH value of bath water is in the acidic region, the function of carbon dioxide to promote the blood circulation is due to the presence of carbon dioxide in the form of a molecular species, contrary to the cases in which the pH value is in the alkaline region where the effect of carbon dioxide would not be altogether exhibited due to the presence of it in the condition of CO₂²⁻-ions or HCO₃⁻-ions.

In order to attain the above-described condition, the carbonate and the acidic substance should be compounded in a selected ratio in which the amount of the carbonate is in the range of, preferably, from 5 to 80% by weight (hereinafter simply termed as %) or, more preferably, from 10 to 50% and the amount of the acidic substance is in the range of, preferably, from 10 to 80% or, more preferably, from 15 to 50% against the total amount though variable according to the kinds of the both components.

The examples of the nicotinic acid derivatives to be incorporated in the weakly acidic bath agent of the invention include methyl nicotinate, ethyl nicotinate and benzyl nicotinate as preferable nicotinates. In more particular, both methyl nicotinate and ethyl nicotinate are the most favorable owing to their prominent function to exhibit the effects of promoting blood circulation and keeping warmth after bathing.

The amount of the nicotinate incorporated in the weakly acidic bath agent of the invention should be in the range of, preferably, from 0.01 to 40% or more preferably, from 0.1 to 4% against the total amount of the bath agent. The bath agent containing less than 0.01% of the nicotinate tends to exhibits an insufficient effect of preventing skin roughening and that containing exceeding 40% of the nicotinate may give a burning sensation to the bathing persons and apt to cause a problem of liking for them.

The bath agent of the invention may further contain additives conventionally used for the prior art bath agents. Such additives include crude (pharmacognostic) drugs, colorants, vitamins, fragrances, enzymes, lanolin, silicone oils, jojoba oil, various kinds of inorganic salts and the like.

The bath agent of the invention is prepared with an adjustment of the constitution by incorporating the above optional components into the mixture of the aforementioned indispensable components to obtain a weak acidity of the bath water when dissolved in the bath water. The preferred form of the bath agent of the invention is granules, tablets, emulsions and the like.

The weakly acidic bath agent of the invention exhibits an excellent effect of bathing owing to the synergistic function of the nicotinates such as prevention or avoiding of skin roughening caused by recurrent bathing and promotion of the blood circulation by carbon dioxide gas present in the bath water.

Then, the present invention is explained in more further detail referring to several examples and comparative examples by no means with an intent of restricting the scope of the invention.

EXAMPLE 1

A weakly acidic bath agent was prepared in a form of a tablet weighing 50 g by stamping using a mixture obtained by well mixing a compound consisting of 30 parts by weight (hereinafter simply referred to as parts) of sodium hydrogen carbonate, 20 parts of succinic acid, 2 parts of ethyl nicotinate, 10 parts of dextrin, 35 parts of sodium sulfate and minute amounts of a colorant and a fragrance.

The aqueous solution containing 0.025% of the above bath agent exhibited a pH value of 6.0.

EXAMPLE 2

A pressure vessel was charged with about 100 liters of a liquid consisting of 10 parts of ethyl alcohol, 10 parts of glycerol, 1 part of methyl nicotinate, 79 parts of purified water and minute amounts of a fragrance and a colorant and filled with carbon dioxide - gas with 8-fold atmospheric pressure followed by standing for one day and night. After the end of the standing period, 2 liters of the liquid was partitioned to be filled in a pressure vessel giving a bath agent.

The aqueous solution containing 0.025% of the above bath agent exhibited a pH value of 6.2.

EXAMPLE 3

A weakly acidic bath agent was prepared in a form of a tablet weighing 50 g by stamping using a mixture obtained by well mixing a compound consisting of 16 parts of sodium carbonate, 32 parts of sodium hydrogen carbonate, 40 parts of succinic acid, 7.7 parts of sodium sulfate, 0.2 part of a fragrance, 0.1 part of a colorant and 4 parts of methyl nicotinate.

The aqueous solution containing 0.025% of the above bath agent exhibited a pH value of 6.2.

EXAMPLE 4

A weakly acidic bath agent was prepared in a form of a tablet weighing 50 g by stamping using a mixture obtained by well mixing a compound consisting of 16 parts of sodium carbonate, 32 parts of sodium hydrogen carbonate, 40 parts of succinic acid, 7.7 parts of sodium sulfate, 0.2 part of a fragrance, 0.1 part of a colorant and 4 parts of ethyl nicotinate.

The aqueous solution containing 0.025% of the above bath agent exhibited a pH value of 6.2.

EXAMPLE 5

A weakly acidic bath agent was prepared in a form of a tablet weighing 50 g by stamping using a mixture obtained by well mixing a compound consisting of 16 parts of sodium carbonate, 32 parts of sodium hydrogen carbonate, 40 parts of succinic acid, 7.7 parts of sodium sulfate, 0.2 part of a fragrance, 0.1 part of a colorant and 4 parts of benzyl nicotinate.

The aqueous solution containing 0.025% of the above bath agent exhibited a pH value of 6.1.

COMPARATIVE EXAMPLE 1

A bath agent was prepared with a similar formulation to Example 1 except that ethyl nicotinate was excluded.

The aqueous solution containing 0.025% of the above bath agent exhibited a pH value of 6.0.

COMPARATIVE EXAMPLE 2

A bath agent was prepared with a similar formulation to Example 2 except that methyl nicotinate was excluded.

The aqueous solution containing 0.025% of the above bath agent exhibited a pH value of 6.2.

COMPARATIVE EXAMPLE 3

A bath agent was prepared in a form of a tablet weighing 50 g by stamping using a mixture obtained by well mixing a compound consisting of 2 parts of ethyl nicotinate, 60 parts of dextrin, 35 parts of sodium sulfate and minute amounts of a colorant and a fragrance.

The aqueous solution containing 0.025% of the above bath agent exhibited a pH value of 7.1.

COMPARATIVE EXAMPLE 4

A bath agent was prepared in a form of a tablet weighing 50 g by stamping using a mixture obtained by well mixing a compound consisting of 4 parts of methyl nicotinate, 95.7 parts of sodium sulfate, 0.1 part of a colorant and 0.2 part of a fragrance.

The aqueous solution containing 0.025% of the above bath agent exhibited a pH value of 7.1.

COMPARATIVE EXAMPLE 5

A bath agent was prepared in a form of a tablet weighing 50 g by stamping using a mixture obtained by well mixing a compound consisting of 16 parts of sodium carbonate, 32 parts of sodium hydrogen carbonate, 40 parts of succinic acid, 11.7 parts of sodium sulfate, 0.2 part of a fragrance and 0.1 part of a colorant.

The aqueous solution containing 0.025% of the above bath agent exhibited a pH value of 6.2.

COMPARATIVE EXAMPLE 6

A bath agent was prepared in a form of a tablet weighing 50 g by stamping using a mixture obtained by well mixing a compound consisting of 16 parts of sodium carbonate, 32 parts of sodium hydrogen carbonate, 5 parts of succinic acid, 4 parts of methyl nicotinate, 47.7 parts of sodium sulfate, 0.2 part of a fragrance and 0.1 part of a coloring matter.

The aqueous solution containing 0.025% of the above bath agent exhibited a pH value of 8.1.

EXAMPLE OF ASSESSMENT (1) Assessment for preventability of skin roughening

Each of the bath agents obtained in Examples 1 to 5 and Comparative Examples 1 to 6 was tested according to the following method.

A human hand is dipped for twenty minutes in an aqueous solution so prepared as to containing 1% of sodium laurylbenzene sulfonate whose temperature is kept at 30° C. Then well washed with water. Thereafter, the hand is dipped for thirty minutes in an aqueous solution containing 0.025% of the relevant bath agent whose temperature is kept at 40° C.

The above procedure is repeated for successive three days each once in a day for a five-person panel. On the fourth day, the condition of the hand of each of the panel members is visually observed and ranked in conformity to the following criterion. The data given in the appended table (1) are the averages for the five members.

5: skin roughening is not observed
4: skin roughening is observed quite slightly
3: skin roughening in a medium degree is observed
2: skin roughening in a fair degree is observed
1: skin roughening in a remarkable degree is observed

TABLE 1

| | Grading for preventing skin roughening (average) |
|---|---|
| Example 1 | 4.9 |
| Example 2 | 4.5 |
| Example 3 | 4.5 |
| Example 4 | 4.6 |
| Example 5 | 4.7 |
| Comparative Example 1 | 1.9 |
| Comparative Example 2 | 2.3 |
| Comparative Example 3 | 2.5 |
| Comparative Example 4 | 2.5 |
| Comparative Example 5 | 1.9 |
| Comparative Example 6 | 2.0 |

(2) Assessment for bathing effect

Five of the bath agents prepared in the examples or comparative examples were subjected to this assessment in which each of the bath agents prepared in Example 1, Comparative Example 1 and Comparative Example 3 was added to the bath in an amount to obtain a concentration of 0.03% in water and each of those prepared in Example 2 and Comparative Example 2 was used in an amount of 2 liters for about 200 liters of the bath water. The concentration of carbon dioxide in each of the bath water thus treated was about 100 ppm.

The bathing effect of these bath water was assessed by each member of a 20-person panel for ten days according to the conventional mode and comments given by them for the assessment on the whole (comprehensive sensation obtained by using), sensation of body warmth, occurence of chill after bathing and sensation of dampishness of the skin were classified in three as shown in Table 2. The numbers shown in the table are the number of the panel members which have given each of the three classified remarks.

TABLE 2

| Comparison | Item of assessment | Agent from Example is better | Not discriminable | Agent from Comparative Exa. is better |
|---|---|---|---|---|
| Comparison between Exa. 1 and Comparative Exa. 1 | Assessment on the whole | 17 | 2 | 1 |
| | Sensation of warmth | 18 | 2 | 0 |
| | Chill after bathing | 19 | 1 | 0 |
| | Sensation of dampishness | 20 | 0 | 0 |
| Comparison between Exa. 1 and Comparative Exa. 3 | Assessment on the whole | 19 | 1 | 0 |
| | Sensation of warmth | 16 | 2 | 2 |
| | Chill after bathing | 13 | 4 | 3 |
| | Sensation of dampishness | 20 | 0 | 0 |
| Comparison between Exa. 2 and Comparative Exa. 2 | Assessment on the whole | 18 | 2 | 0 |
| | Sensation of warmth | 18 | 1 | 1 |
| | Chill after bathing | 19 | 1 | 0 |
| | Sensation of dampishness | 19 | 1 | 0 |

(3) Effects of promoting blood circulation and keeping warmth

Various measurements were carried out against each of the members of a three-person panel before and after bathing for 10 minutes in any of the baths of 150 liters water kept at 40° C. each containing a tablet of the bath agent prepared in Example 3 or Comparative Examples 4 to 6.

Measurements of the blood flow volume were carried out using a laser-doppler blood flowmeter (PERIFLUX) and measurements of the skin-surface temperature were carried out using a thermograph (manufactured by Nippon Electric Manufacturing Company). Every measurement was carried out in a room kept at 25° C.

The results of the measurements were as shown in Table 3 (blood flow volume measured at inside of forearms) and Table 4 (temperature of skin surfaces) as the average values for three panel members.

TABLE 3

Blood Flow Volume
(Relative values on the basis of the values before bathing (=1)) n = 3

| Kind of agent | After 20 minutes | After 40 minutes | After 60 minutes |
|---|---|---|---|
| Example 3 | 2.6 | 2.3 | 1.9 |
| Comparative Exa. 4 | 2.1 | 1.7 | 1.4 |
| 5 | 2.2 | 1.9 | 1.5 |
| 6 | 2.1 | 1.8 | 1.5 |

TABLE 4

Temperature of Skin Surface (°C.)

| Kind of agent | Before bathing | After 20 minutes | After 40 minutes | After 60 minutes |
|---|---|---|---|---|
| Example 3 | 33.7 | 35.8 | 35.4 | 35.0 |
| Comparative Exa. 4 | 33.6 | 34.8 | 34.6 | 33.9 |
| 5 | 33.7 | 35.2 | 34.6 | 34.2 |
| 6 | 33.7 | 34.9 | 34.6 | 33.9 |

As being made obvious by the above-described testing results, the weakly acidic bath agent provided by the present invention is superior as compared with the conventional bath agents for comparison in every viewpoint.

What is claimed is:

1. A weakly acidic bath agent comprising 5 to 80% by weight of carbon dioxide or a carbon dioxide-generating substance and 0.01 to 40% by weight of a derivative of nicotinic acid represented by the general formula:

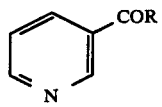

wherein R represents a group $-OR_1$, in which $R_1$ is a saturated or an unsaturated hydrocarbon group having 1 to 10 of carbon atoms, or benzyl group.

2. The weakly acidic bath agent as claimed in claim 1, wherein said hydrocarbon group is selected from a group consisting of a methyl group and an ethyl group.

3. The weakly acidic bath agent as claimed in claim 1, wherein said derivative of nicotinic acid is compounded in an amount in the range of from 0.1 to 4% by weight to the total amount.

4. The weakly acidic bath agent as claimed in claim 1, wherein said carbon dioxide-generating substance is a combination of a carbonate and an acidic substance.

5. The weakly acidic bath agent as claimed in claim 4, wherein said carbonate is selected from the group consisting of sodium hydrogen carbonate, sodium sesquicarbonate, sodium carbonate, potassium carbonate, ammonium hydrogen carbonate, magnesium carbonate and calcium carbonate.

6. The weakly acidic bath agent as claimed in claim 5, wherein said acidic substance is selected from the group consisting of organic acids and inorganic acids.

7. The weakly acidic bath agent as claimed in claim 6, wherein said organic acid is selected from the group consisting of succinic acid, glutaric acid, adipic acid, pimelic acid, fumaric acid, glutamic acid, asparaginic acid, malic acid, citric acid, ascorbic acid, benzoic acid, and pyrrolidone carboxylic acid.

8. The weakly acidic bath agent as claimed in claim 4, wherein said carbonate is compounded in an amount in the range of from 5 to 80% by weight and said acidic substance is compounded in an amount in the range of from 10 to 80% by weight of the total amount of said bath agent.

9. The weakly acidic bath agent as claimed in claim 8, wherein said carbonate is compounded in an amount in the range of from 10 to 50% by weight and said acidic substance is compounded in an amount in the range of from 15 to 50% by weight of the total amount of said bath agent.

* * * * *